United States Patent [19]

Rosner

[11] 4,288,620

[45] Sep. 8, 1981

[54] PROCESS FOR THE PRODUCTION OF 4-ACYLAMIDO-2-NITRO-1-ALKOXYBEN-ZENES

[75] Inventor: Manfred Rosner, Muttenz, Switzerland

[73] Assignee: Ciba-Geigy AG, Basel, Switzerland

[21] Appl. No.: 158,977

[22] Filed: Jun. 12, 1980

[30] Foreign Application Priority Data

Jun. 21, 1979 [CH] Switzerland .......................... 5806/79

[51] Int. Cl.³ .................. C07C 102/00; C07C 102/04
[52] U.S. Cl. .................................... 564/144; 564/142; 564/143; 564/223
[58] Field of Search ................ 564/223, 143, 142, 144

[56] References Cited

U.S. PATENT DOCUMENTS 3,149,032  9/1964  Waring ................................ 424/324

FOREIGN PATENT DOCUMENTS 2448132  4/1976  Fed. Rep. of Germany .

*Primary Examiner*—Arthur P. Demers
*Attorney, Agent, or Firm*—Sprung, Felfe, Horn, Lynch & Kramer

[57] ABSTRACT

A process for the production of 4-acylamido-2-nitro-1-alkoxybenzenes by acylating p-alkoxyaniline with an acylating agent to 4-acylamido-alkoxybenzenes and subsequently nitrating these latter to 4-acylamido-2-nitro-1-alkoxybenzenes, which process comprises carrying out the reaction in an inert solvent, without isolation of the intermediates, using 88 to 95% sulfuric acid in the weight ratio of 6:1 to 10:1, based on the p-alkoxyaniline employed, during the nitration step.

8 Claims, No Drawings

PROCESS FOR THE PRODUCTION OF 4-ACYLAMIDO-2-NITRO-1-ALKOXYBENZENES

The present invention relates to a process for the production of 4-acylamido-2-nitro-1-alkoxybenzenes by acylating p-alkoxyaniline with an acylating agent to 4-acylamido-alkoxybenzenes and subsequently nitrating these latter to 4-acylamido-2-nitro-1-alkoxybenzenes, which process comprises carrying out the reaction in an inert solvent, without isolation of the intermediates, using 88 to 95% sulfuric acid in the weight ratio of 6:1 to 10:1, based on the p-alkoxyaniline employed, during the nitration step.

The reaction proceeds in accordance with the following scheme:

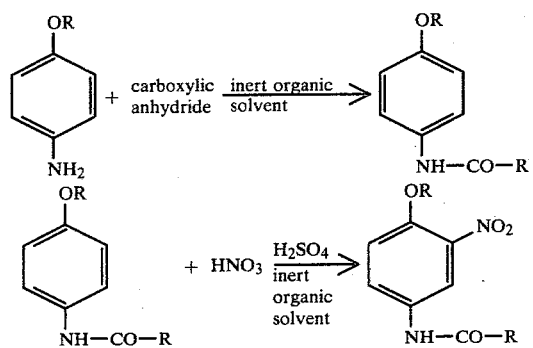

wherein $R = CH_3, C_2H_5, C_3H_7$.

In accordance with the old method, the reaction is carried out in two steps:

(1) p-Anisidine in the melt is charged into water, followed by acylation in aqueous emulsion and crystallisation of 4-acylamido-anisole. The product is collected by filtration, washed and dried. It is absolutely essential to remove the water used as solvent after the first reaction step, as this water would dilute the reagents too heavily in the second step.

(2) The 4-acylamido-anisole obtained is added to 98 to 100% sulfuric acid at a temperature below 0° C., whereupon nitration with nitric acid or nitrosulfuric acid is effected at a temperature below 0° C. Working up is effected by precipitating the product by pouring the reaction mass into ice-water.

The drawback of this process is that, after the first reaction step, the intermediate must be worked up and the nitration in the second step carried out at a temperature below 0° C. It has been observed that losses in yield occur if the process is carried out at temperatures above 0° C. and/or if the dissolving time of the intermediate in sulfuric acid monohydrate is prolonged.

On account of the high cooling requirement, however, very long dissolving and nitrating times are necessary in the old method. The lengthy duration of the second reaction step, the long sojourn time of the acyl derivative in the acid during the addition of sulfuric acid and during the nitration, results in large-scale sulfonation of the acylamido-anisoles. In pilot plant production, the drop in yield is about 15% (from 90% to about 75% of theory in a 0.5 kmole batch), while in production on an industrial scale an even greater drop in yield must be assumed on account of the longer cooling times expected.

Although the danger of sulfonation of the acylalkoxybenzene in monohydrate at temperatures below 0° C. is still relatively slight, it cannot be neglected. At temperatures of 10° C. and more, this secondary reaction causes a substantial loss in yield. On the other hand, the sojourn time of the acylalkoxybenzene in sulfuric acid is of decisive importance, for which reason as rapid a dissolving as possible is required. It is therefore necessary to provide for a rapid removal of heat by effective cooling. The following table gives a brief summary of results which were obtained for e.g. 4-acetamidoanisole in monohydrate, without organic solvent, at different temperatures and employing the old method.

TABLE 1

Influence of the dissolving temperature and dissolving time of 4-acetamido-anisole in monohydrate on the yield

| solvent sulfuric acid | dissolving temperature °C. | time min. | nitration temperature °C. | time min. | yield % of theory |
|---|---|---|---|---|---|
| monohydrate | up to 0° | 30 | 20–25° | 30 | 83 |
| monohydrate | 10–15° | 30 | 20–25° | 30 | 73 |
| monohydrate | 25–30° | 30 | 25–30° | 30 | 56 |
| monohydrate | up to 0° | 240 | 20–25° | 180 | 76 |

It has been found to be all the more surprising that, if the reaction is carried out in an inert organic solvent as reaction medium:

(1) the reaction can be carried out continuously in the same reaction vessel from start to finish without isolation of the intermediate, (2) the reaction conditions, especially as regards the nitration temperature, are not to be considered as crucial.

The use of sulfuric acid having a concentration of about 92% instead of monohydrate as well as the addition of e.g. chlorobenzene as inert organic solvent as claimed in the novel process reduce the danger of sulfonation considerably. The dissolving temperature can therefore freely be raised. For example, no diminution of yield or quality resulted from carrying out the dissolving step at 20° to 25° C. and even at about 40° C. over the course of 3 hours.

For the nitration itself it is advisable to maintain lower temperatures; but temperatures of 0° to 25° C. suffice and even those of up to 30° C. are still entirely possible. Noticeable losses in yield and quality only occur at temperatures above about 35° C.

Suitable inert organic solvents for the novel process are in particular nonpolar organic solvents, e.g. aliphatic and aromatic chlorinated hydrocarbons, aliphatic hydrocarbons etc.

The amount of inert organic solvent can vary within wide limits and is necessary in particular for better stirrability and heat removal. As, however, some 95% can be recovered and re-used without further processing, the quantity of solvent only has a certain importance as regards the production capacity. An advantageous ratio of solvent to substrate is from 3:1 to 8:1.

After initiation of the acylation reaction, the temperature is allowed to rise adiabatically and heat is then removed by cooling only at about 50° to 70° C. When the acylation reaction has been brought to completion, which is advantageously accomplished with carboxylic acid anhydrides in approximately stoichiometric amounts, although suitable acylating agents are also corresponding acid chlorides or carboxylic acids, the reaction mixture is cooled to about 30° C. and, without isolation of the 4-acylamido-alkoxide obtained as intermediate, 88 to 95% sulfuric acid is added in the weight ratio 6:1 to 10:1, based on p-alkoxyaniline, while keeping the temperature during this time (about 30 minutes) at about 25° to 40° C.

The amount and concentration of the sulfuric acid are of great importance. Under the given conditions, a sulfuric acid concentration in the range from about 88 to 95% has been found most suitable. Both higher and lower concentrations result in a substantial loss in yield.

Table 2 summarises results using different concentrations of acid and indicates by-product obtained.

TABLE 2

Yields and purity of 4-acetamido-2-nitroanisole using different concentrations of $H_2SO_4$ (batches of 1 mole/833 g $H_2SO_4$)

| Concentration of $H_2SO_4$ % | Yield % of theory | Content of the isolated product in % (GC) | | | |
|---|---|---|---|---|---|
| | | 2-$NO_2$ | 3-$NO_2$ | Di-$NO_2$ | 4-acet. |
| 80 | 44.3 | 60.9 | 38.9 | — | — |
| 85 | 72.0 | 89.4 | 9.9 | — | — |
| 88 | 87.7 | 97.0 | 2.0 | — | — |
| 90 | 89.9 | 97.3 | 1.6 | — | 0.1 |
| 92.2 | 90.2 | 98.6 | 0.7 | 0.1 | 0.1 |
| 93 | 89.8 | 98.9 | 0.5 | 0.1 | 0.2 |
| 96 | 84.9 | 98.5 | 0.4 | 0.3 | 0.1 |
| 98 | 77.4 | 97.3 | 0.3 | 0.4 | 0.8 |
| 100 | 69.2 | 95.9 | 0.2 | 1.5 | 0.9 |

2-$NO_2$ : 4-acetamido-2-nitroanisole
3-$NO_2$ : 4-acetamido-3-nitroanisole
Di-$NO_2$ : 4-acetamido-2,5-dinitroanisole
4-acet : 4-acetamido-anisole As may be required, the amount of sulfuric acid can be reduced to somewhat below 800 g/mole. However, the lower limit should be kept to between 650 and 750 g/mole if the formation of the 3-nitro derivative is not to be encouraged, as Table 3 shows.

TABLE 3

Yields and by-products obtained using different amounts of sulfuric acid (batches with 92.2% acid)

| Amount of $H_2SO_4$ in g/mole based on p-anisidine | Yield % of theory | Content of the isolated product in % (gas chromatography) | | | |
|---|---|---|---|---|---|
| | | 2-$NO_2$ | 3-$NO_2$ | Di-$NO_2$ | 4-acet. |
| 833 | 90.2 | 98.6 | 0.7 | 0.1 | 0.1 |
| 800 | 90.5 | 98.0 | 1.1 | 0.1 | 0.1 |
| 700 | 91.8 | 98.4 | 0.8 | — | — |
| 625 | 87.7 | 96.9 | 2.7 | — | — |
| 430 | 58.2 | 77.3 | 22.4 | — | — |

Aside from poorer yields, the losses of chlorobenzene are a few percent higher as a result of poorer separation when using 700 g and less $H_2SO_4$/mole of batch.

With further cooling, during which the temperature should not exceed 35° C., 62.3% nitric acid is then added in stoichiometric amounts up to a possible 5% excess. The reaction is complete after about 30 minutes, including addition time. The completeness of the reaction to the formation of 4-acylamido-2-nitro-alkoxybenzene is tested by thin-layer chromatography.

The theoretical requirement of $HNO_3$ is 100% per mole of product employed. An excess of nitric acid results in the formation of by-products and should be avoided. However, the concentration of $HNO_3$ in the range from 60 to 65% and somewhat above and below is variable without any significant difference.

After the nitration the product is worked up by phase separation. The aqueous phase contains the product, which is precipitated by pouring this phase into ice-water, then filtered, suspended, neutralised with ammonia, collected by filtration and, if desired, dried. The solvent phase is used again in a further batch.

In order to test the efficacy of the novel process in respect of constant product and yield quality, both the dissolving time of the intermediate in the sulfuric acid/solvent mixture and the nitration time were each extended repeatedly to 4 hours at about 25° C. The result was a drop in yield of only just 3% while still attaining a purity of about 97%. This test shows the very clear superiority of the novel process over the old one if a comparison is made with the values reported previously in Table 1 above.

In addition to the surprising advantages referred to above, the nonel process affords additional advantages, namely:

(a) Under the conditions of the solvent process it is possible to use a sulfuric acid of much lower concentration, namely 88 to 95% acid instead of monohydrate. The consequence is that virtually no more sulfonation occurs and, allied thereto, higher yields and fewer by-products are obtained.

(b) The changed reaction conditions permit the reaction to be carried out at much higher temperature without the occurrence of secondary reactions, whereby the removal of heat is also facilitated. A change-over from expensive brine-cooling to water-cooling is also possible.

(c) The substantially better heat removal makes it possible to conduct the reaction more quickly, which in turn results in improved quality and yield in comparison with the old process.

(d) A substantial saving in energy is achieved on account of the only insignificant cooling requirement.

(e) Ecological advantages accrue from eliminating the working up procedure of the first reaction step.

(f) The process is suitable for continuous operation on account of the advantageous time-temperature relations.

The compounds obtained by the novel process are valuable dyestuff intermediates, e.g. those disclosed in U.S. Pat. No. 3,652,534, which are used e.g. for the production of azo dyes.

The following Examples illustrate the novel process.

EXAMPLE 1

A 2.5 liter flask is charged with 800 g of chlorobenzene. With stirring, 123.2 g of 100% p-anisidine (preferably as melt) are then added. Then 102 g of acetic anhydride are added dropwise in the course of about 15 minutes, whereupon the temperature rises to 65° C. After stirring for 15 minutes at 65° C., the mixture is cooled to about 30° C. within about 10 minutes using a cooling bath, whereupon beige-coloured crystals of the acetanisidide begin to precipitate in the temperature range from about 45° C. The resultant suspension is slightly viscous, but readily stirrable. The addition of 800 g of 92% sulfuric acid is then commenced, with care being taken that the temperature does not much exceed 30°-40° C. The addition takes about 10 minutes. With further cooling, the addition of 101.2 g of 62.3% $HNO_3$ is commenced immediately at a maximum temperature of 25° C. During the addition, the temperature can be allowed to rise to 20°-25° C. With the first few drops of $HNO_3$ the emulsion starts becoming fluid immediately and the original blue colour changes to brown. The addition is complete after about 10 minutes and the batch is stirred for 20 minutes at 20° to 25° C. until the reaction is complete. The reaction mixture is then charged into a 2 liter separating funnel, whereupon a lower, dark-brown layer separates immediately. The upper, chlorobenzene layer is usually colourless or only a faintly yellow colour. The lower layer is then passed slowly into a glass beaker, into which a mixture of 300 g of ice and water is stirred. The temperature is kept at around +5° C. by the constant addition of altogether about 1500 g of ice. A thick yellow suspension is finally obtained. The suspension is stirred and then filtered. The filter cake is washed with 350 ml of ice-water, well pressed and, if desired, dried. Mother liquor and wash water are combined. The amount of chlorobenzene remaining in the separating funnel is about 760 g and, after replenishment to the original amount, can be re-used in the next batch. Yield: about 193 to 195 g of 4-acetamido-2-nitro-anisole in 97-98% purity. Melting point: about 150°-151° C.

The product obtained by this method is sufficiently pure to be reacted in a subsequent synthesis step to give 3-benzylamino-4-methoxyacetanilide.

EXAMPLE 2

The procedure of Example 1 is repeated using 130.1 g of propionic anhydride instead of acetic anhydride as acylating agent and gasoline as reaction medium. Yield: 215 g of 4-propionamido-2-nitro-anisole with a melting point of 104°-105° C.

EXAMPLE 3

The procedure of Example 1 is repeated using the corresponding molar amount of p-ethoxyaniline instead of p-anisidine, acetic anhydride as acylating agent, and o-dichlorobenzene as inert organic solvent. 4-Acetamido-2-nitro-1-ethoxybenzene is obtained in the same good purity and yield as in Example 1.

EXAMPLE 4—CONTINUOUS PROCESS

A storage vessel is charged with 400 g of petroleum spirit with a boiling range of 110°-140° C. and 123.2 g of p-anisidine (preferably as melt). The resultant solution is acylated by gradually running in 130.1 g of propionic anhydride, in the course of which the temperature may rise to about 70° C. The solution is then advantageously cooled to room temperature and then 800 g of 95% sulfuric acid are added. The addition of $H_2SO_4$ can be made both discontinuously in a cooled vessel and continuously in a reactor equipped with a heat exchanger. The temperature during the addition should not rise much above 30°-35° C. The heterogeneous reaction mixture is then passed continuously through a reactor cooled with brine (e.g. flow pipe) and into which 102 g of 62.3% nitric acid (based on the substrates to be nitrated) are added continuously. The rate of flow through the reactor is adjusted to the cooling capacity such that the nitration mixture which exits has a temperature of 20°-25° C. The reaction mixture (total volume: 1250 ml) is collected in a separator trap, whereupon two phases again separate. The upper phase (petroleum spirit) is almost colourless and continuously decanted. It can be re-used without processing (amount recovered: about 390 g). The lower, inorganic phase is poured continuously into 2 liters of a mixture of water and ice, whereupon the product precipitates in the form of yellow crystals. The precipitate is washed and dried, affording c. 215 g (c 92% of theory) of 2-nitro-4-propionamido-anisole with a melting point of c. 105° C. Purity: c. 96-97%.

What is claimed is:

1. A process for the production of 4-acylamido-2-nitro-1-alkoxybenzenes by acylating p-alkoxyaniline with an acylating agent to 4-acylamido-alkoxybenzenes and subsequently nitrating these latter to 4-acylamido-2-nitro-1-alkoxybenzenes, which process comprises carrying out the reaction in an inert solvent, without isolation of the intermediates, using 88 to 95% sulfuric acid in the weight ratio of 6:1 to 10:1, based on the p-alkoxyaniline employed, during the nitration step.

2. A process according to claim 1 for the production of compounds of the formula

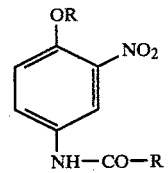

wherein R is $CH_3$, $C_2H_5$ or $C_3H_7$.

3. A process according to claim 1, wherein the inert organic solvent is a nonpolar organic solvent.

4. A process according to claim 1, wherein the inert organic solvent is chlorobenzene or o-dichlorobenzene or gasoline.

5. A process according to claim 1, which comprises acylating p-anisidine with acetic anhydride or propionic anhydride in chlorobenzene as inert organic solvent, then adding to the batch, after acylation, the 6.5-fold amount, based on p-anisidine, of 92% sulfuric acid at 0° to 25° C. and subsequently nitrating with 62.3% nitric acid at 0° to 25° C. and, after phase separation, working up the product from the aqueous phase in conventional manner and recycling the separated organic solvent to a further batch.

6. A process according to claim 1, wherein the acylating agent is a carboxylic acid anhydride, carboxylic acid or carboxylic acid chloride which contains 1 to 3 carbon atoms.

7. A process according to claim 1, wherein the acylating agent is a carboxylic acid anhydride.

8. A process according to claim 1 which is carried out continuously.

* * * * *